(12) United States Patent
Chattopadhyay et al.

(10) Patent No.: US 9,493,475 B2
(45) Date of Patent: Nov. 15, 2016

(54) TEXTILE TREATMENT COMPOUNDS AND COMPOSITIONS

(71) Applicant: Devan Chemicals NV, Ronse-Renaix (BE)

(72) Inventors: Subrata Chattopadhyay, Bankura (IN); Martin Moeller, Aachen (DE); Helmut Keul, Aachen (DE); Maxime Durka, Ronse (BE); James Budzynski, Belper (GB)

(73) Assignee: DEVAN CHEMICALS NV, Ronse-Renaix (BE)

(*) Notice: Subject to any disclaimer, the term of this patent is extended or adjusted under 35 U.S.C. 154(b) by 0 days.

(21) Appl. No.: 14/426,561

(22) PCT Filed: Sep. 5, 2013

(86) PCT No.: PCT/EP2013/068404
§ 371 (c)(1),
(2) Date: Mar. 6, 2015

(87) PCT Pub. No.: WO2014/044547
PCT Pub. Date: Mar. 27, 2014

(65) Prior Publication Data
US 2015/0218177 A1    Aug. 6, 2015

(30) Foreign Application Priority Data
Sep. 18, 2012 (GB) .................................. 1216638.5

(51) Int. Cl.
| | | |
|---|---|---|
| *C08G 65/333* | (2006.01) | |
| *C08G 65/337* | (2006.01) | |
| *C07D 487/10* | (2006.01) | |
| *C08G 65/325* | (2006.01) | |
| *D06M 15/61* | (2006.01) | |
| *D06M 16/00* | (2006.01) | |
| *C08G 65/24* | (2006.01) | |
| *D06M 13/463* | (2006.01) | |
| *D06M 13/513* | (2006.01) | |
| *D06M 15/53* | (2006.01) | |
| *C08G 65/20* | (2006.01) | |
| *C08G 65/26* | (2006.01) | |

(52) U.S. Cl.
CPC ............ *C07D 487/10* (2013.01); *C08G 65/20* (2013.01); *C08G 65/24* (2013.01); *C08G 65/263* (2013.01); *C08G 65/325* (2013.01); *C08G 65/337* (2013.01); *C08G 65/33317* (2013.01); *D06M 13/463* (2013.01); *D06M 13/513* (2013.01); *D06M 15/53* (2013.01); *D06M 15/61* (2013.01); *D06M 16/00* (2013.01); *C08G 2650/50* (2013.01); *D06M 2200/20* (2013.01); *D06M 2200/35* (2013.01); *D06M 2200/50* (2013.01)

(58) Field of Classification Search
CPC .. C08G 65/24; C08G 65/337; C08G 65/325; C08G 65/33317; C08G 2650/36; D06M 13/463; D06M 13/513; D06M 15/61; D06M 125/53; D06M 16/00; D06M 2200/20; D06M 2200/35
See application file for complete search history.

(56) References Cited

U.S. PATENT DOCUMENTS

| | | |
|---|---|---|
| 3,917,817 A | 11/1975 | Vanlerberghe et al. |
| 3,949,014 A | 4/1976 | Maki et al. |

(Continued)

FOREIGN PATENT DOCUMENTS

| | | |
|---|---|---|
| EP | A 0 414 377 | 2/1991 |
| FR | 2162025 | 11/1972 |

(Continued)

OTHER PUBLICATIONS

International Search Report issued for International PCT Application No. PCT/EP2013/068404, dated May 27, 2014.

(Continued)

*Primary Examiner* — Anthony J Green
(74) *Attorney, Agent, or Firm* — K&L Gates LLP (57) ABSTRACT

A cationic polymer is disclosed, represented by: A) wherein "$P^1$" and "$P^2$" represent portions of the cationic polymer to which the first functional group shown in A is bonded, or B) wherein "P" represents the remainder of the cationic polymer to which the second functional group shown in B is bonded, or the cationic polymer may comprise one or more of the first functional groups as shown in A and/or one or more of the second functional groups as shown in B where X represents an anion, typically chlorine. The cationic polymers are useful as textile softeners and for enhancing substantivity and durability of active compounds co-deposited onto textiles with the cationic polymers. Also provided is a method for forming said cationic polymer, a textile treatment composition and a textile treated with said textile treatment composition.

A)

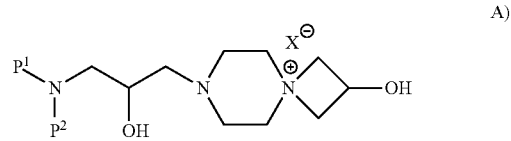

B)

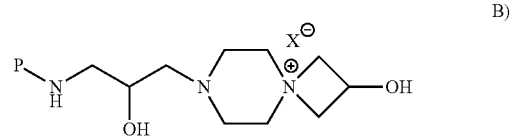

20 Claims, 2 Drawing Sheets

(56) References Cited

U.S. PATENT DOCUMENTS

| | | |
|---|---|---|
| 4,240,450 A | 12/1980 | Grollier et al. |
| 2005/0060812 A1 | 3/2005 | Batchelor et al. |

FOREIGN PATENT DOCUMENTS

| | | |
|---|---|---|
| WO | WO 92/07132 | 4/1992 |
| WO | WO 97/42287 | 11/1997 |
| WO | WO 98/29530 | 7/1998 |
| WO | WO 00/15748 | 3/2000 |
| WO | WO 01/25386 | 4/2001 |
| WO | WO 03/059967 | 7/2003 |

OTHER PUBLICATIONS

Search Report dated Jan. 11, 2013 issued for the corresponding UK patent application No. GB1216638.5.

Search Report dated Sep. 18, 2013, issued for the corresonding Belgian patent application No. 201200654.

Marton-Meresz M et al: "Synthesis of Cytostatically Active Piperazine Derivatives", Acta Chimica Hungarica, 1983, 112 (1), pp. 31-41.

Subrata Chattopadhyay et al., "Functional Polymers Bearing Reactive Azetidinium Groups..", Macromolecular Chemistry and Physics, vol. 213, No. 5, Mar. 16, 2012, p. 500-512.

TEXTILE TREATMENT COMPOUNDS AND COMPOSITIONS

CROSS-REFERENCE TO A RELATED APPLICATION AND PRIORITY CLAIM

This application claims the benefit under 35 U.S.C. §371 to International Application Number PCT/EP2013/068404 filed on 5 Sep. 2013 which claims the priority of United Kingdom Patent Application No. 1216638.5 filed on 18 Sep. 2012 to which priority is also claimed by the present application. The entire disclosures of said applications are incorporated by reference herein for all purposes.

TECHNICAL FIELD

The invention relates to cationic polymers for use in textile treatment compositions for treatment of fibres, yarns, fabrics, textiles or garments and to related methods of preparation of the cationic polymers from pre-polymers. The cationic polymers are of use as textile softeners and for increasing substantivity and tenacity, durability or longevity of other compounds co-applied with the cationic polymers onto textiles.

BACKGROUND

Many textile treatment compositions are known in the prior art, involving the use of polymeric materials for treatment of fibres, yarns, fabrics, textiles or finished garments during the manufacturing process. Such treatments may be used in the fabric or garment supply chain to modify the "finish" of fabrics, garments or textile components. The polymeric materials may be substantively bound to the textile or textile components to confer specific characteristics to the resulting fabric or garment which persist through multiple laundering cycles in use, such as easy-iron, soft handle, permanent crease, soil release, antimicrobial activity and the like.

Throughout the specification, the term "textile" is used to include textile components, textiles and fabrics or garments prepared from a textile, so for instance the term "textile" as used herein encompasses fibres, yarns, fabrics, textiles or finished garments or upholstered articles. Textiles may be prepared by knitting, weaving or the like, or may be non-woven textiles such as textiles prepared by fibre-entanglement methods such as are well-known in the prior art.

Cationic polymers are of particular use in textile treatment compositions as cationic functional groups in the polymers may cross-link or react with textile substrates through the cationic functional groups and chemical bonds may be formed between the cationic polymers and the textile fibres or between the cationic molecules themselves or with other molecules co-deposited with the cationic polymers. Such polymers may be useful both in laundering compositions and in industrial textile treatment processes. When used in laundry compositions, the polymer substantivity may be poorer than when used in industrial treatment processes, which may typically involve post-application heat treatment (such as curing at temperatures up to 150° C. or more). However, such cationic polymers are also of use in laundry applications which do not involve post-application heat treatment; for instance on fabric conditioner compositions used for post-laundering treatment of textile articles.

Detergent compositions containing polyamide-polyamine fabric treatment agents for laundry use are described in the international patent application publications WO 98/29530 and WO 97/42287.

A process for treating fibres is disclosed in U.S. Pat. No. 3,949,014. This describes the use of a polyamine/epichlorohydrin resin as a binder, together with an amphoteric high molecular weight compound having at least two cationic groups and at least two anionic groups per molecule.

Compositions containing an amino functional polymer to impart shrink resistance to wool are known. See, for instance, EP-A-0 414 377. WO 92/07132 discloses softening treatments for textiles which involve the deposition of cationic polymers formed from quaternisation of polyetheramines and the like.

International application WO 03/059967 discloses an azetidinium functionalised polymer containing primary or secondary amine groups for use in textile treatment compositions, where the polymer containing primary or secondary amine groups is epihalohydrin-modified to form azetidinium groups.

SUMMARY OF THE INVENTION

Typical cationic polymers containing azetidinium may be formed by reaction of a polymer having primary and/or secondary amine groups with a coupling compound such as epichlorohydrin (1-chloro-2,3-epoxypropane). The resulting cationic polymers contain some azetidinium and epichlorohydrin functional groups. Other epihalohydrins may be used as coupling compounds. The term "coupling compound" is used to mean a compound which is capable of reacting with primary and/or secondary amine groups of a pre-polymer in order to convert the amine groups into functional groups having a quaternary nitrogen group or an otherwise reactive group.

The resulting cationic polymers may bond, cross-link or react with textiles or other compounds as a result of the functional groups. During curing, covalent bonds may be formed between cationic polymers and fibres of textiles and between cationic polymer molecules themselves or with other molecules present.

The use of cationic polymers bearing the azetidinium group as part of the cationic functional group can impart many benefits to fabrics, particularly those containing cellulosic materials (such as cotton). These benefits may include improved wear resistance, improved handle or feel, reduced pilling, improved colour definition, reduced wrinkling, soft feel and improved perfume substantivity and longevity.

A problem with the use of epichlorohydrin, or other epihalohydrins, as a "coupling compound" for formation quaternary nitrogen groups on pre-polymers, by reaction with amine functional groups already present in the pre-polymers, is that it is believed that the charged azetidinium group is only formed reliably on secondary amine groups (i.e. mid-chain amines). The primary amine groups (i.e. terminal amine groups) are thought to react to form an amino-chloropropanol functional group which is capable of rearranging, under certain conditions, to form an azetidine group.

It is postulated that azetidine and/or azetidinium groups are responsible for the high reactivity of the cationic polymers towards textile fibres and for the effectiveness of the cationic polymers in increasing performance and durability of co-applied compounds such as antimicrobials and the like. Hence, it is desirable to provide a cationic polymer in which the azetidinium groups are reliably formed following reaction of the primary and secondary amines of a pre-polymer.

It is one object of the invention, amongst others, to provide cationic polymers which have azetidinium groups present as part of the cationic groups under a broad range of conditions. It is a further object of the invention to provide methods of forming cationic polymers which do not involve the direct reaction of epihalohydrin with a pre-polymer, because of the complex safety precautions required in handling epihalohydrins. Hence, it is an object of the invention to provide a process involving use of a coupling compound capable of reacting with a pre-polymer to form a cationic polymer including azetidinium groups.

A further object of the invention is to provide textile treatment compositions for deposition of active compounds onto textiles using the cationic polymers as deposition and durability aids.

A first aspect of the invention provides a cationic polymer represented by

A)

wherein $P^1$ and $P^2$ represent portions of the cationic polymer to which the first functional group shown in A is bonded,

B)

wherein P represents the remainder of the cationic polymer to which the second functional group shown in B is bonded, or a cationic polymer comprising one or more of the first functional groups as shown in A and/or one or more of the second functional groups as shown in B,
wherein "X" is an anion.

A second aspect of the invention provides a coupling compound according to the formula:

C)

wherein "$X^1$" is a leaving group, such as a halogen, and "X" is an anion. The cationic polymer of the first aspect of the invention may be prepared by reaction of the coupling compound with a pre-polymer comprising one or more primary and/or secondary amine groups.

A third aspect of the invention provides a method of forming a coupling compound according to the second aspect of the invention, the method comprising reacting epihalohydrin with piperazine, in a suitable molar ratio to generate the coupling compound, wherein the epihalohydrin provides "$X^1$" and "X" as halogens.

A fourth aspect of the invention provides a method of forming a cationic polymer according to the first aspect of the invention by reacting a pre-polymer comprising one or more primary and/or secondary amine groups with a coupling compound according to the second aspect of the invention.

A fifth aspect of the invention provides a textile treatment composition comprising a cationic polymer according to the first aspect of the invention dispersed and/or dissolved in a solvent.

A sixth aspect of the invention provides a method of treatment of a textile comprising applying a textile treatment composition according to the fifth aspect of the invention to the textile, whereby the cationic polymer and any antimicrobial compound are substantially deposited onto the textile.

DETAILED DESCRIPTION OF THE INVENTION

Throughout this specification, the term "comprising" or "comprises" means including the component(s) specified but not to the exclusion of the presence of others. The term "consisting essentially of" or "consists essentially of" means including the components specified but excluding other components except for materials present as impurities, unavoidable materials present as a result of processes used to provide the components, and components added for a purpose other than achieving the technical effect of the invention. Typically, a composition consisting essentially of a set of components will comprise less than 5% by weight, typically less than 3% by weight, more typically less than 1% by weight of non-specified components.

Whenever appropriate, the use of the term "comprises" or "comprising" may also be taken to include the meaning "consists essentially of" or "consisting essentially of" and also the meaning "consists of" or "consisting of".

Where molecular weight is referred to in relation to polymers in this specification, it means number average molecular weight as measured by GPC (gel permeation chromatography) in tetrahydrofuran at 25° C. with calibration against polystyrene standards.

The term "aqueous solution" is used herein is meant to signify that the solution referred to predominantly has water as solvent, typically with at least 70% by weight, such as 80% by weight or 90% by weight of the solvent being water.

It is to be understood that the various features set out below in relation to the various, different aspects of the invention are not to be considered as restricted to use with any specific aspect of the invention. Where appropriate, such features are to be considered as applicable to any other aspect of the invention where the feature would be appropriate and so it would be evident that the corresponding use of the feature is to also be considered as disclosed. So, for instance, preferred features in relation to polyether blocks for the cationic polymer of the invention are also implicitly disclosed in relation to the pre-polymers which may be used to prepare the cationic polymers by reaction with the coupling compound of the invention.

The first aspect of the invention provides a cationic polymer represented by:

A)

wherein "$P^1$" and "$P^2$" represent portions of the cationic polymer to which a first functional group as shown in A is bonded,

B)

wherein "P" represents the remainder of the cationic polymer to which a second functional group as shown in B is bonded,
or a cationic polymer comprising one or more of the first functional groups as shown in A and/or one or more of the second functional groups as shown in B,
wherein "X" represents an anion.

The cationic polymer may have only one of these functional groups per molecule, or may have any suitable combination of functional groups A and B. It is to be understood that the portions of the cationic polymer, "$P^1$" and "$P^2$", shown in formula A may include further first or second functional groups of types shown in A or B. Typically, the first functional group shown in A may be a mid-chain group and the second functional group shown in B may be a terminal group. By "mid-chain group" it is meant that the quaternary nitrogen of the functional group A will be part of the backbone of the polymer of which it forms a part. As will be explained below, the first functional group in A may be derived from a secondary amine group of a pre-polymer whereas the second functional group in B may be derived from a primary amine group of a pre-polymer.

It should be understood that although the azetidinium group is shown on one side of the piperazine structure of the functional groups (furthest from the terminal nitrogen), the functional groups may be capable of internal rearrangement.

Although the cationic polymer of the first aspect of the invention may be a linear polymer, the invention is not limited to linear polymers and the cationic polymer may be a branched polymer arrangement.

The anion "X" may be any suitable monovalent or multivalent anion or mixture of such similar or dissimilar anions, such as a monovalent anion based on halogen or an anion based on an anion-forming leaving group, such as $CH_3SO_3^-$ (methosulphate (mesylate) in anion form), $CH_3C_6H_4SO_3^-$ (tosylate in anion form) or the like, or a mixture thereof. The anion "X" may be monatomic, such as a halogen anion, or polyatomic, such as a sulphate anion ($SO_4^{2-}$). Preferably, the anion "X" is a halogen, more preferably chlorine ($Cl^-$). Typically, the anion "X" may be based on the same atom or group as the anion-forming leaving group "$X^1$" of the coupler molecule of the second aspect of the invention, in which case "$X^1$" may be also preferably be a halogen or mixture of halogens, such as chlorine. Chlorine is preferred because of its reactivity combined with the widespread commercial availability of chlorine-based reagents.

The cationic polymer may suitably have a backbone or polymer chain comprising polyether, polyester, polyamide blocks or the like. Preferably, the backbone comprises polyether blocks. In one preferred arrangement, the backbone may comprise two or more polyether blocks, each mutually linked through the terminal nitrogen of a first functional group as shown in A and the cationic polymer may be terminated by second functional groups as shown in B.

The polyether blocks in such an arrangement may, for example, be poly(ethylene oxide) blocks (PEO), poly(propylene oxide) blocks (PPO) or polytetrahydrofuran blocks (PTHF—also referred to as poly(tetramethylene oxide)). Each polyether block may comprise from say 5 to 500 monomers and combinations of different polyether blocks may be present within the cationic polymer of the invention.

In a preferred cationic polymer according to the invention, the polyether blocks may be polytetrahydrofuran blocks of formula: $—[C_4H_8O]_n—$, where n is an integer and wherein each block has a number average molecular weight of from 250 to 3,000 Dalton (a Dalton being the same as 1 g per mole). The number of polymer blocks may be one or two, or, for instance three or more, particularly in branched polymer arrangements. The blocks may be linked by one or more first functional groups as shown in A, or other suitable linking groups may be employed.

Preferably, the cationic polymer of the invention has a number average molecular weight of from 300 to 1,000,000 Dalton.

The second aspect of the invention provides a coupling compound according to the formula:

C)

wherein "$X^1$" is a leaving group, such as a halogen, and "X" is an anion.

It will be understood that "X" may represent a single monovalent or multivalent anion or a mixture of such similar or dissimilar anions. The anion "X" may be any suitable anion or mixture of anions, such as a monovalent anion based on halogen or based on a leaving group, such as $CH_3SO_3^-$ (methosulphate (mesylate) in anion form), $CH_3C_6H_4SO_3^-$ (tosylate in anion form) or the like, or a mixture thereof. Preferably, the anion "X" is a halogen, more preferably chlorine. The anion "X" may be monatomic, such as a halogen anion, or polyatomic, such as a sulphate anion ($SO_4^{2-}$).

"$X^1$" is an anion-forming leaving group. It is to be understood that the term "leaving group" as used herein also includes atoms, such as halogen atoms, as leaving group. "$X^1$" may be any suitable anion-forming leaving group, such as $CH_3SO_3$ (methosulphate), $CH_3C_6H_4SO_3$ (tosylate) or is preferably a halogen or mixture of halogens. Most preferably, "$X^1$" is chlorine.

Typically, the anion "X" may be an anion of the same halogen or leaving group as the anion-forming leaving group "$X^1$" of the coupler molecule of the second aspect of the invention, in which case "$X^1$" may be a leaving group, such as $CH_3SO_3$ (methosulphate), $CH_3C_6H_4SO_3$ (tosylate) or preferably a halogen or mixture of halogens. Most preferably, "$X^1$" is chlorine.

The coupling compound of this second aspect of the invention may be formed by reacting epihalohydrin with piperazine, in a suitable molar ratio to generate the desired compound, such as a molar ratio of about 1.5:1 or more, such as about 2:1. The third aspect of the invention provides this method of preparation of the coupling compound.

Suitably, the epihalohydrin and piperazine may be reacted in aqueous solution at a temperature of 50° C. or less to provide an aqueous solution of the coupling compound.

The cationic polymer of the first aspect of the invention may be prepared by reaction of the coupling compound of the second aspect of the invention with a pre-polymer comprising one or more primary and/or secondary amine groups. Hence, a fourth aspect of the invention provides a method of forming a cationic polymer according to the first aspect of the invention by reacting a pre-polymer, comprising one or more primary and/or secondary amine groups, with a coupling compound according to the second aspect of the invention. This reaction is suitably carried out in aqueous solution. The temperature of reaction is preferably kept below the boiling point of the solution, such as 95° C. or less and reaction may be allowed to proceed for a period from 2 to 8 hours.

Suitably, the pre-polymer may be a polyetheramine. The term "polyetheramine" as used herein includes polymers having a backbone or polymer chain comprising one or more polyether blocks with the polymer blocks terminated by primary amine groups and/or linked through secondary amine groups. In one preferred arrangement, the backbone may comprise two or more polyether blocks, each mutually linked through a secondary amine and terminated by primary amines.

The polyether blocks in such an arrangement may be as set out hereinbefore in relation to the cationic polymer of the first aspect of the invention.

In a preferred pre-polymer according to the invention, the polyether blocks may be polytetrahydrofuran blocks of formula: —$[C_4H_8O]_n$—, where n is an integer and wherein each block has a number average mean molecular weight of from 250 to 3,000 Dalton. The number of polymer blocks may be one or two, or, for instance three or more, particularly in branched polymer arrangements. Such pre-polymers are commercially available from Huntsman Corporation under the trade names Jeffamine™ (PPO/PEO-based polyetheramines) or Elastamine™ (PTHF-based polyetheramines).

The fifth aspect of the invention provides a textile treatment composition comprising a cationic polymer according to the first aspect of the invention dispersed and/or dissolved in a solvent.

The solvent may be selected from water, methanol, ethanol, isopropanol and mixtures thereof. Suitably, the solvent is an aqueous solvent, preferably water.

The use of the cationic polymers of the invention in textile treatment compositions may be used to impart many benefits to fabrics, particularly those containing cellulosic materials (such as cotton) including improved wear resistance, improved handle or feel, reduced pilling, improved colour definition, reduced wrinkling and soft feel. The textile treatment composition may further comprise one or more other active ingredients for co-deposition along with the cationic polymer of the invention, and the substantivity and longevity/durability of the active ingredient(s) on the textile may be enhanced by co-deposition with the cationic polymer of the invention. Such active ingredients may include, for instance, perfumes, fragrances, stabilizers, such as anti-oxidants or acid scavengers, clarifying agents, colouring agents, anti-UV-agents, antistatic agents, flame retardants, microcapsules, cyclodextrins, inorganic nanoparticles, other functional polymers, antimicrobial compounds and the like.

It has been found that the cationic polymer of the invention may be of use for enhancing the substantivity, and longevity of antimicrobial compounds, and the textile treatment composition may further comprise an antimicrobial compound.

The antimicrobial compound for use with the cationic polymer of the invention may suitably be a silylated quaternary ammonium compound according to the formula:

D)

wherein "$R_1$" and "$R_2$" are independently selected from $CH_3$ and H, "$R_4$" is $C_2H_5$, $CH_3$ or H, "Z" is a bridging group selected from $CH_2$, $C_2H_4$ and $C_3H_6$, "X" is an anion or mixture of anions as already set out hereinbefore for "X", preferably a halogen, more preferably chlorine, and "m" is an integer from 11 to 21, preferably from 15 to 19, more preferably 17.

A suitable textile treatment composition may comprise:
from 0.1 to 1.0%, such as from 0.2 to 0.7%, by weight of cationic polymer, and
from 0.01 to 0.5%, such as from 0.1 to 0.4%, by weight of antimicrobial compound,
dispersed and/or dissolved in a solvent, preferably an aqueous solvent.

The sixth aspect of the invention provides a method of treatment of a textile comprising applying a textile treatment composition according to the fifth aspect of the invention to the textile, whereby the cationic polymer and any antimicrobial compound are substantially uniformly deposited onto the textile.

By "substantially uniformly" it is meant that the total level of the compounds from the textile treatment composition is approximately the same to within ±10% at any particular location on the textile to which the composition has been applied. Deposition may be investigated using the following test:
cut a 1.0 g sample of each of a treated textile and a (comparative) untreated textile;
place each of the samples into an individual container which contains 50 mL of a 0.001% concentration bromophenol blue solution (available from, e.g. Sigma-Aldrich);
shake each container vigorously for 10 minutes;
remove each sample and rinse in warm water for 2 minutes, prior to drying.

The presence, and uniformity of presence, of both cationic polymer and antimicrobial compound may be easily determined visually by the fabric being stained blue. A treated textile sample will be appear to have been coloured blue to the naked eye, whilst the untreated sample will not have any blue colouration.

The method of treatment of this aspect of the invention suitably provides from 0.05 to 1.0% by weight, such as 0.1 to 0.7%, preferably from 0.2 to 0.6%, by weight of the cationic polymer deposited on the textile, expressed as a percentage by weight of the treated dry textile. When the silylated quaternary ammonium compound as antimicrobial compound is also included in the textile treatment composition, suitably from 0.01 to 0.5% by weight of silylated quaternary ammonium compound is deposited on the textile per kg of textile.

Preferably, the textile treatment composition of the invention, is substantially uniformly applied to a textile to provide a treated textile, and the treated textile is dried to substantially remove the solvent of the textile treatment composition. For instance, drying may be achieved by the application of heat to the treated textile. Suitably the temperature of the treated textile is kept below 100° C., more preferably below 60° C., even more preferably below 50° C., whilst the treated textile is dried.

The treatment composition of the invention may suitably be applied by spraying, padding, dip coating, soaking or by passing the textile through a bath of the treatment composition. Application may be effected as either a continuous process or a batch process and may be performed at any stage in the processing of the textile (e.g. by treating fibres or yarn prior to weaving or knitting or by treating a textile sheet or a finished garment).

For industrial treatment of textiles, for instance prior to formation of a textile into a garment, or treatment of a garment prior to sale or use, heat treatment may be applied to the treated textile in order to cure the treated textile. Such heat treatment may involve temperatures at or in excess of 100° C., such as in the range 100° C. to say 200° C., for instance up to 170° C.

EXAMPLES

Embodiments of the present invention will now be described, by way of example only.

Figure 1:
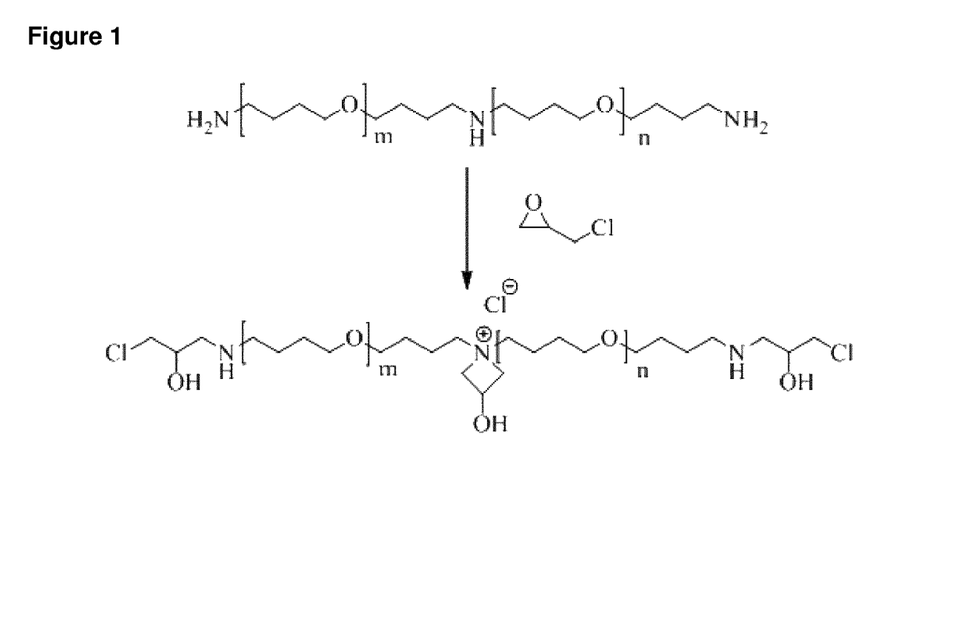
FIG. 1 shows a reaction scheme for the formation of a prior art cationic polymer.
Figure 2:
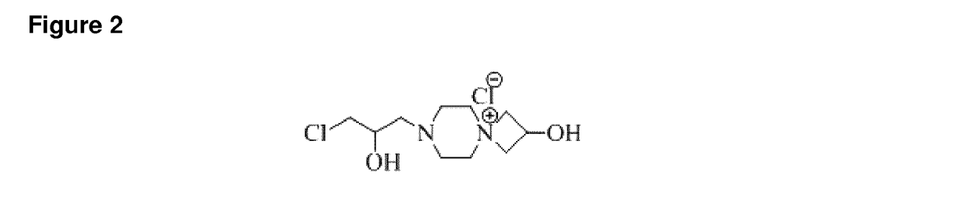
FIG. 2 shows the coupling compound of the second aspect of the invention.
Figure 3:
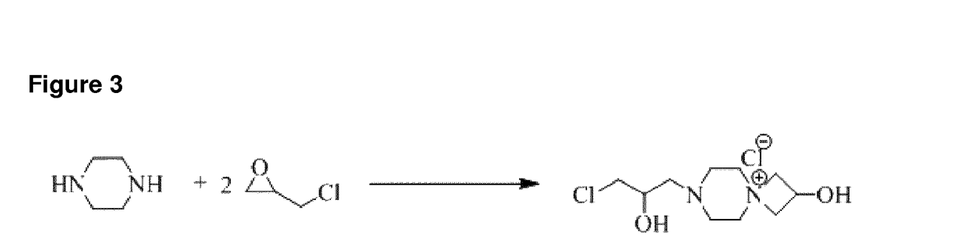
FIG. 3 shows a reaction scheme for the formation of the coupling compound of the second aspect of the invention, according to the third aspect of the invention (Example 2)
Figure 4:
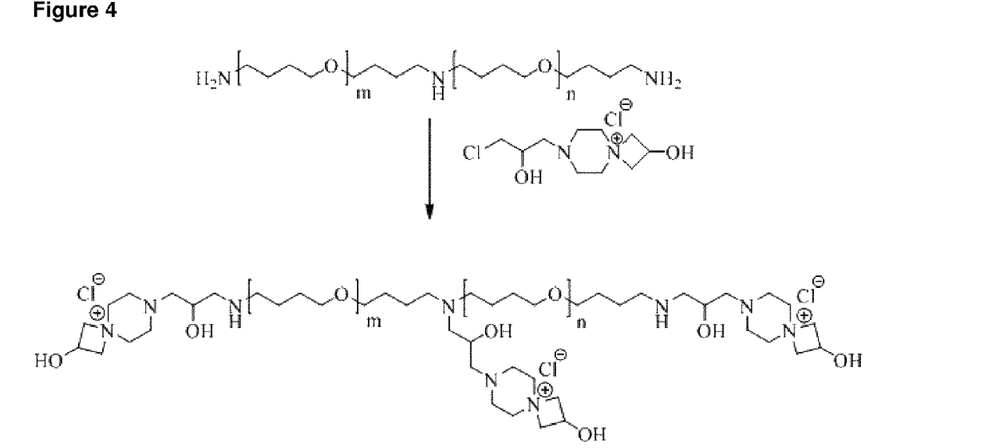
FIG. 4 shows a reaction scheme for the formation of an embodiment of a cationic polymer according to the invention (Example 2)
Figure 5:
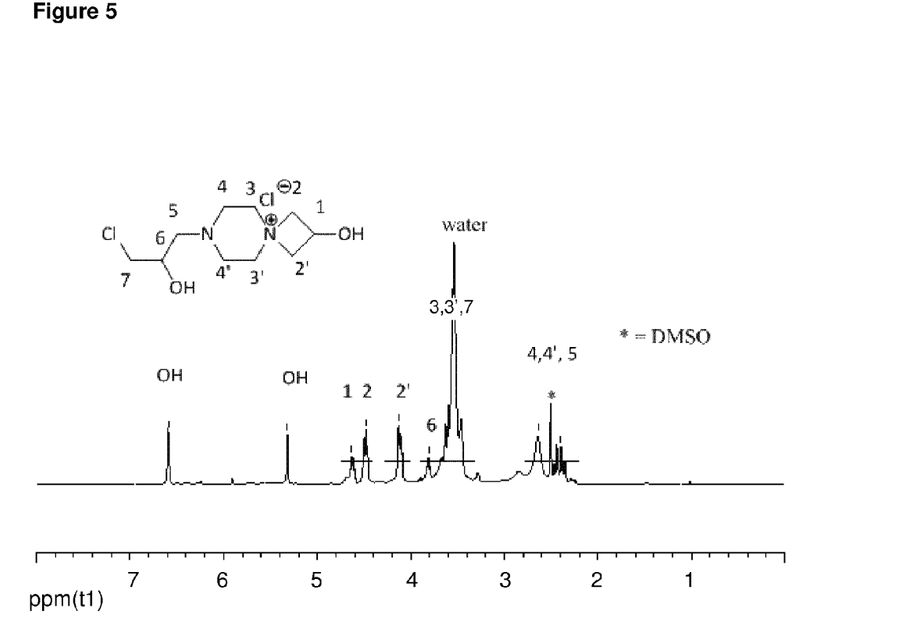
FIG. 5 shows the $^1$H-NMR spectrum of the coupling compound of the second aspect of the invention.

FIG. 1 shows a reaction scheme for the formation of a prior art cationic polymer, FIG. 2 shows the coupling compound of the second aspect of the invention, FIG. 3 shows a reaction scheme for the formation of the coupling compound of the second aspect of the invention, according to the third aspect of the invention (Example 2), FIG. 4 shows a reaction scheme for the formation of an embodiment of a cationic polymer according to the invention (Example 2), and FIG. 5 shows the $^1$H-NMR spectrum of the coupling compound of the second aspect of the invention.

Turning to FIG. 1, this reaction scheme shows a linear pre-polymer of the Elastamine™ type, specifically Elastamine™1700, having two PTHF polymer blocks (with n having a value such that the molecular weight of the pre-polymer is about 1700) linked through a linking group comprising a secondary amine group. The polymer chain has primary amine groups at each end.

Reaction with epichlorohydrin at a temperature of 70° C. in the presence of sodium hydroxide results in the formation of a known prior art cationic polymer having an azetidinium group formed at the secondary amine group of the pre-polymer and with amino-chloropropanol groups at the terminal amine groups of the pre-polymer. Although the amino-chloropropanol groups may be capable of rearrangement into azetidinium structures under certain conditions, this is not always the case for such prior art polymers.

FIG. 2 shows the chemical structure of the coupling compound of the second aspect of the invention, with $X^1$ and $X^-$ as chlorine, this coupling compound being capable of reaction with a pre-polymer in order to form the cationic polymer of the invention, with the resulting cationic polymer having azetidinium groups present in the resulting functional groups formed by reaction with primary or secondary amines.

Example 1

The preparation of the coupling compound is straightforward and can be achieved under mild reaction conditions to provide a high quantitative yield of the desired product. FIG. 3 shows a reaction scheme involving the combination of 1 mole of piperazine in with 2 moles of epichlorohydrin resulting in the formation of the coupling compound. The reaction can be carried out at room temperature, say 25° C., or at 50° C. or less over a period of about 48 hours, or in shorter times if the reaction is heated to a temperature such as in excess of 50° C., or up to 80° C., or even up to 95° C. The resulting coupling compound is soluble in water and the reaction may be carried out in the water or in aqueous solution to generate a solution containing up to 25% by weight of the coupling molecule in water. For instance, 8.1% by weight of piperazine may be reacted with 17.4% by weight of piperazine in the presence of 74.5% by weight of water. In a typical suitable reaction procedure, the water is charged into mixing vessel and agitation commenced. Piperazine is then added to the mixing vessel and agitation continued until the piperazine is dissolved. This will typically take about 30 minutes at room temperature. Epichlorohydrin is then added to the mixing vessel at a sufficiently low rate to ensure that the temperature does not increase excessively to cause boiling. Cooling may be used in order to assist with this. Typically, the epichlorohydrin may be added over a period of about 60 minutes. The resulting mixture is then blended together for about 2 hours and then allowed to stand for about 48 hours without further mixing.

Example 2

Turning to FIG. 4, this reaction scheme shows the same linear pre-polymer of the Elastamine™1700 type as used in the reaction scheme shown in FIG. 1, but in this case the reaction proceeds using the coupling compound rather than epichlorohydrin. Reaction with the coupling compound (in this particular example at a temperature of 90° C. over a period of 5 hours) and results in the formation of an embodiment of a cationic polymer according to the invention having azetidinium groups formed at the secondary amine group of the pre-polymer and also at the terminal amine groups of the pre-polymer. The azetidinium structures are present in the cationic polymer of the invention without requiring any special conditions and it is thought that the presence of these groups over a broad range of conditions provides improved performance for such polymers according to the first aspect of the invention.

FIG. 5 shows the $^1$H-NMR spectrum for the coupling compound, demonstrating the presence of the azetidinium group and confirming the structure of the coupling compound.

Example 3

Example 3 (no corresponding Figure) demonstrates the benefits achievable for improved longevity of antimicrobial activity using co-deposition onto textile with a cationic polymer according to an aspect of the invention. The cationic polymer according to the invention, prepared in accordance with Example 2 was compared with the prior art polymer prepared in the manner set out for FIG. 1. Both the inventive cationic polymer CPI (Example 2) and the comparative cationic polymer CPC (FIG. 1) were based upon a pre-polymer Elastamine™1700, reacted with the coupling compound of formula C in the case of the cationic polymer according to the invention, and reacted with epichlorohydrin in the case of the comparative cationic polymer.

A textile treatment composition was prepared comprising the cationic polymer (either CPI or CPC) in combination with an antimicrobial quaternary silane according to formula D (Aegis AEM 5772-5: a 3.6% solution of 3(trimethoxysilyl)propyldimethyloctadecyl ammonium chloride available from Aegis Environments USA) and the composition was applied to a polyester fabric by padding to give a loading of 0.49% by weight polymer and 0.22% by weight of antimicrobial on substrate (expresses as a proportion of the weight of the dried treated textile).

After heating to dryness of the treated textile (carried out at a drying temperature of about 100° C.—any suitable temperature such as from 90 to 200° C. may be used to provide adequate drying speed without risk of polymer degradation), bacterial reduction studies were carried out before and after a number of washes to simulate industrial launderings typical for hospital applications. The wash conditions used were according to EN ISO 6330:2000 with wash type 5A conditions, but with the wash carried out at 75° C. rather than the 40° C. set out in the standard. The results are shown in Table 1, which shows very high bacterial reductions results, even after more than 100 wash cycles. The results are given as an antimicrobial reduction after 24 hours of exposure in accordance with ASTM-2149-01.

TABLE 1

| Number of Washes | CPC + Antimicrobial (Comparative) | CPI + Antimicrobial (Invention) |
|---|---|---|
| 0 | 99.99% | 99.99% |
| 50 | 99.99% | 99.99% |
| 100 | 96.9% | 97.3% |

It will be appreciated that modifications to the above described examples may be made without departing from the scope of the invention as defined in the appended claims. For example, the pre-polymer used may be a polyetheramine of the PEO or PPO type, rather than a PTHF-based polyetheramine.

The described and illustrated embodiments are to be considered as illustrative and not restrictive in character, it being understood that preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

The invention claimed is:

1. A cationic polymer represented by:

A)

wherein "$P^1$" and "$P^2$" represent portions of the cationic polymer to which a first functional group shown in A is bonded, the cationic polymer having a backbone or polymer chain comprising polyether or polyester blocks; or

B)

wherein "P" represents a remainder of the cationic polymer to which a second functional group shown in B is bonded, wherein "X" represents an anion; or a cationic polymer comprising:

a) one or more of a first functional group as shown in A

A)

wherein "$P^1$" and "$P^2$" represent portions of the cationic polymer to which the first functional group shown in A is bonded, and one or more of a second functional group as shown in B,

B)

wherein "P" represents a remainder of the cationic polymer to which the second functional group shown in B is bonded; or b) one or more of a second functional group as shown in B, wherein "P" represents a remainder of the cationic polymer to which the second functional group shown in B is bonded, wherein "X" represents an anion.

2. A cationic polymer according to claim 1 wherein "X" is chlorine.

3. A cationic polymer according to claim 1 wherein the cationic polymer has a backbone comprising polyether blocks.

4. A cationic polymer according to claim 3 wherein the backbone comprises two or more polyether blocks, each mutually linked through the terminal nitrogen of a first functional group as shown in A and the cationic polymer is terminated by second functional groups as shown in B.

5. A cationic polymer according to claim 4 wherein the polyether blocks are polytetrahydrofuran blocks of formula: —[$C_4H_8O$]$_n$—, where n is an integer and wherein each block has a number average mean molecular weight of from 250 to 3,000 Dalton.

6. A cationic polymer according to claim 1 having a number average molecular weight of from 300 to 1,000,000 Dalton.

7. A method of forming a cationic polymer according to claim 1 by reacting a pre-polymer comprising one or more primary and/or secondary amine groups with a coupling compound according to the formula wherein "X" is an anion and "$X^1$" is a leaving group.

8. The method of claim 7 wherein the pre-polymer is a polyetheramine.

9. A method according to claim 7, wherein X" and "$X^1$" are each chlorine.

10. A textile treatment composition comprising a cationic polymer according to claim 1 dispersed and/or dissolved in a solvent.

11. A textile treatment composition according to claim 10 wherein the solvent is selected from the group consisting of water, methanol, ethanol, isopropanol and mixtures thereof.

12. A textile treatment composition according to claim 11, wherein the solvent is water.

13. A method of forming a coupling compound according to the formula wherein "X" is an anion and "$X^1$" is a leaving group comprising reacting epihalohydrin with piperazine, in a suitable molar ratio to generate the coupling compound, wherein the epihalohydrin provides "X" and "$X^1$" as halogen.

14. A method according to claim 13 wherein the epihalohydrin and piperazine are reacted in aqueous solution at a temperature of 50° C. or less to provide an aqueous solution of the coupling compound.

15. A method according to claim 13, wherein "X" and "$X^1$" are chlorine.

16. A textile treatment composition comprising:
a cationic polymer dispersed and/or dissolved in a solvent; and
an antimicrobial compound,
wherein the cationic polymer is represented by:

wherein "$P^1$" and "$P^2$" represent portions of the cationic polymer to which a first functional group shown in A is bonded, wherein "P" represents the remainder of the cationic polymer to which a second functional group shown in B is bonded, or wherein the cationic polymer comprises one or more of the first functional groups as shown in A and/or one or more of the second functional groups as shown in B, wherein "X" represents an anion.

17. A textile treatment composition according to claim 16, wherein the antimicrobial compound is a silylated quaternary ammonium compound according to the formula:

wherein "$R_1$" and "$R_2$" are independently selected from the group consisting of $CH_3$ and H, "$R_4$" is $C_2H_5$, $CH_3$ or H, "Z" is a bridging group selected from $CH_2$, $C_2H_4$ and $C_3H_6$, "X" is an anion, and "m" is an integer from 11 to 21.

18. A textile treatment composition according to claim 16 comprising:
from 0.1 to 1.0 percent by weight of cationic polymer, and
from 0.01 to 0.5 percent by weight of antimicrobial compound,
dispersed and/or dissolved in a solvent.

19. A textile treatment composition according to claim 17, wherein "m" is an integer from 15 to 19.

20. A method of treatment of a textile comprising applying a textile treatment composition comprising a cationic polymer dispersed and/or dissolved in a solvent to the textile whereby the cationic polymer and an antimicrobial compound are substantially uniformly deposited onto the textile, wherein the cationic polymer is a) a cationic polymer represented by:

A)

wherein "P$^1$" and "P$^2$" represent portions of the cationic polymer to which a first functional group shown in A is bonded; or

B)

wherein "P" represents a remainder of the cationic polymer to which a second functional group shown in B is bonded, or b) a cationic polymer comprising one or more of the first functional groups as shown in A and/or one or more of the second functional groups as shown in B, wherein "X" represents an anion.

* * * * *